United States Patent
Smith et al.

(10) Patent No.: US 9,651,442 B2
(45) Date of Patent: May 16, 2017

(54) ULTRASONIC MEASUREMENT

(71) Applicant: The Lubrizol Corporation, Wickliffe, OH (US)

(72) Inventors: Oliver Smith, Chesterland, OH (US); Michael R. Sutton, Matlock (GB)

(73) Assignee: The Lubrizol Corporation, Wickliffe, OH (US)

( * ) Notice: Subject to any disclaimer, the term of this patent is extended or adjusted under 35 U.S.C. 154(b) by 185 days.

(21) Appl. No.: 14/407,675

(22) PCT Filed: Jun. 26, 2013

(86) PCT No.: PCT/US2013/047810
§ 371 (c)(1),
(2) Date: Dec. 12, 2014

(87) PCT Pub. No.: WO2014/004620
PCT Pub. Date: Jan. 3, 2014

(65) Prior Publication Data
US 2015/0168243 A1  Jun. 18, 2015

Related U.S. Application Data

(60) Provisional application No. 61/664,973, filed on Jun. 27, 2012.

(51) Int. Cl.
*G01L 11/04* (2006.01)
*G01L 11/06* (2006.01)
(Continued)

(52) U.S. Cl.
CPC ............ *G01L 11/06* (2013.01); *G01N 29/024* (2013.01); *G01D 5/48* (2013.01); *G01L 9/0025* (2013.01);
(Continued)

(58) Field of Classification Search
CPC ..................................................... G01L 9/0025
(Continued)

(56) References Cited

U.S. PATENT DOCUMENTS

| 2012/0152022 A1* | 6/2012 | Schatz | G01L 11/06 73/632 |
| 2015/0168243 A1* | 6/2015 | Smith | G01L 11/06 73/703 |

FOREIGN PATENT DOCUMENTS

| CN | 1587943 A | 3/2005 | |
| DE | 102009026968 | * 12/2009 | G01L 11/06 |
| DE | 102009026968 A1 | 12/2009 | |

OTHER PUBLICATIONS

PCT/US2013, 'Written Opinion of the International Searching Authority', Jun. 27, 2012, 4 pages.*

(Continued)

*Primary Examiner* — Clayton E Laballe
*Assistant Examiner* — Kevin Butler
(74) *Attorney, Agent, or Firm* — Christopher D. Hilker; David M. Shold; Teresan W. Gilbert

(57) ABSTRACT

A fluid 10 is contained within a chamber 12. The chamber wall 14 has an inner surface 16 exposed to the fluid 10 and an outer surface 18 separated from the inner surface 18 by the material 20 of the wall 14. Ultrasound 22 is introduced into the material 20. Measurement of the time of flight of the ultrasound 22 through the body 20 allows a measurement to be made of the pressure of the fluid 10.

20 Claims, 3 Drawing Sheets

(51) Int. Cl.
   *G01N 29/024* (2006.01)
   *G01L 9/00* (2006.01)
   *G01D 5/48* (2006.01)
(52) U.S. Cl.
   CPC .......... *G01L 9/0091* (2013.01); *G01L 9/0092* (2013.01); *G01L 11/04* (2013.01); *G01N 2291/02872* (2013.01); *G01N 2291/102* (2013.01)
(58) Field of Classification Search
   USPC .......................................................... 73/703
   See application file for complete search history.

(56) References Cited

OTHER PUBLICATIONS

PCT/US2013, 'International Search Report', Nov. 19, 2013, 3 pages.*

* cited by examiner

ULTRASONIC MEASUREMENT

The present invention relates to ultrasonic measurement and in particular, but not exclusively, to methods and apparatus for making measurements by means of ultrasound.

Ultrasound consists of a wave of mechanical disturbance which propagates through a body of material at a frequency higher than the typical upper limit for human hearing (around 20 kHz). Ultrasound waves will propagate through many different materials, including fluids (liquid or gas) and solids. In particular, ultrasound typically propagates well through bodies of many metals. Ultrasound will reflect at surfaces of bodies, and at interfaces between different materials. The speed at which ultrasound will propagate through a material is dependent on the physics of the material and is generally known as the acoustic velocity or the speed of sound.

Examples of the present invention provide a method of measuring the pressure of a contained fluid, the fluid being contained in a chamber which is defined, at least in part, by a wall having an inner surface exposed to the fluid within the chamber, and an outer surface separated from the inner surface by the material of the wall, the method comprising:

introducing ultrasound into the material of the wall at an introduction position;

detecting the ultrasound after travelling through the material of the wall to a detection position;

measuring the time of flight of the detected ultrasound from the introduction position to the detection position;

and providing a measurement of the fluid pressure at the inner surface, as a function of the measured time of flight.

The fluid pressure measurement may be provided by comparison of the time of flight measurement with previously calibrated measurements of fluid pressure and time of flight.

The ultrasound may be introduced at one surface and travel to the other surface. The ultrasound may reflect from the other surface and be detected at the said one surface. The ultrasound may be introduced at the outer surface.

The material of the wall may be metal. The wall and chamber may form part of a machine or machine component. The machine or machine component may comprise one or more of a combustion chamber, a bearing, a gearbox and a cam arrangement. The fluid may be a lubricant, compression fluid or actuator fluid.

Other examples of the present invention provide apparatus comprising a chamber which, in use, contains fluid, the chamber being defined, at least in part, by a wall having an inner surface exposed to the fluid within the chamber, and an outer surface separated from the inner surface by the material of the wall, the apparatus further comprising:

an ultrasound transducer arrangement operable to introduce ultrasound into the material of the wall at an introduction position and to detect the ultrasound after travelling through the material of the wall to a detection position; and a control arrangement operable to measure the time of flight of the detected ultrasound from the introduction position to the detection position and to provide a measurement of the fluid pressure at the inner surface, as a function of the measured time of flight.

The fluid pressure measurement may be provided by comparison of the time of flight measurement with previously calibrated measurements of fluid pressure and time of flight.

The ultrasound may be introduced at one surface and travel to the other surface. The ultrasound may reflect from the other surface and be detected at the said one surface. The ultrasound may be introduced at the outer surface.

The material of the wall may be metal. The wall and chamber may form part of a machine or machine component. The machine or machine component may comprise one or more of a combustion chamber, a bearing, a gearbox and a cam arrangement. The fluid may be a lubricant, compression fluid or actuator fluid.

Examples of the invention also provide apparatus for use with a chamber which, in use, contains fluid, the chamber being defined, at least in part, by a wall having an inner surface exposed to the fluid within the chamber, and an outer surface separated from the inner surface by the material of the wall, the apparatus comprising:

an ultrasound transducer arrangement operable to introduce ultrasound into the material of the wall at an introduction position and to detect the ultrasound after travelling through the material of the wall to a detection position; and a control arrangement operable to measure the time of flight of the detected ultrasound from the introduction position to the detection position and to provide a measurement of the fluid pressure at the inner surface, as a function of the measured time of flight.

Examples of the present invention will now be described in more detail, by way of example only, and with reference to the accompanying drawings, in which:

FIG. 1 is a highly simplified and schematic diagram of ultrasound propagating in a body of material;

FIG. 2 corresponds with FIG. 1, illustrating a measuring method according to one example of the present invention;

OVERVIEW

Figure 1:
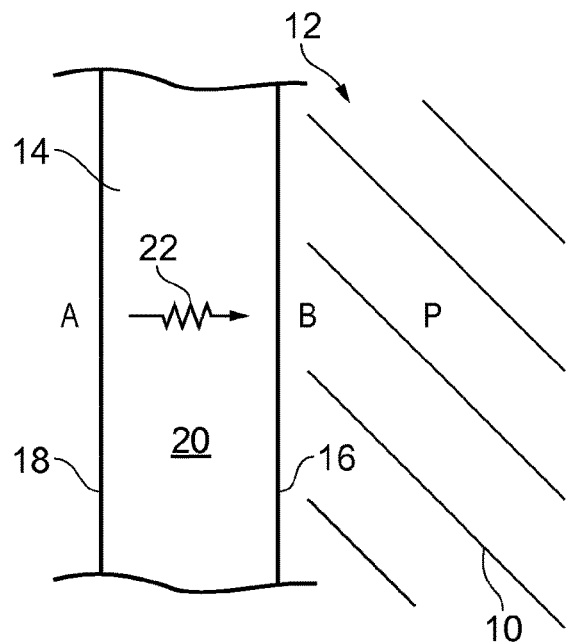

FIG. 1 is a simple diagram illustrating a fluid 10 (diagonal hatching) contained within a chamber 12. The whole of the chamber 12 is not shown in FIG. 1. The chamber is defined, at least in part, by a wall 14 which has an inner surface 16 exposed to the fluid 10 within the chamber 12. The wall 14 also has an outer surface 18 separated from the inner surface 16 by the material 20 of the wall.

A pulse of ultrasound is indicated at 22. The ultrasound is created by a transducer (not illustrated in FIG. 1) at an introduction position A on the outer surface 18, and is shown propagating through the body 20 to a detection position B on the inner surface 16. The following description explains that the time of flight of the ultrasound 22 through the body 20 (the material of the wall 14) depends on the nature of the material and on the environmental conditions of the body 20. In particular, the time of flight from the introduction position to the detection position depends on the pressure exerted on the inner surface 16 by the fluid 10. Accordingly, the examples demonstrate the provision of a measurement of the fluid pressure at the inner surface 16, as a function of the time of flight measurement of the ultrasound 22 through the body 20.

In particular, the fluid pressure measurement can be provided by comparison of the time of flight measurement with previously calibrated measurements of fluid pressure and time of flight. The previously calibrated measurements may also be calibrated against temperature or any other effect which will cause a change in the time of flight. Further explanation of these issues is set out below in relation to FIG. 3.

EXAMPLE 1

Figure 2:
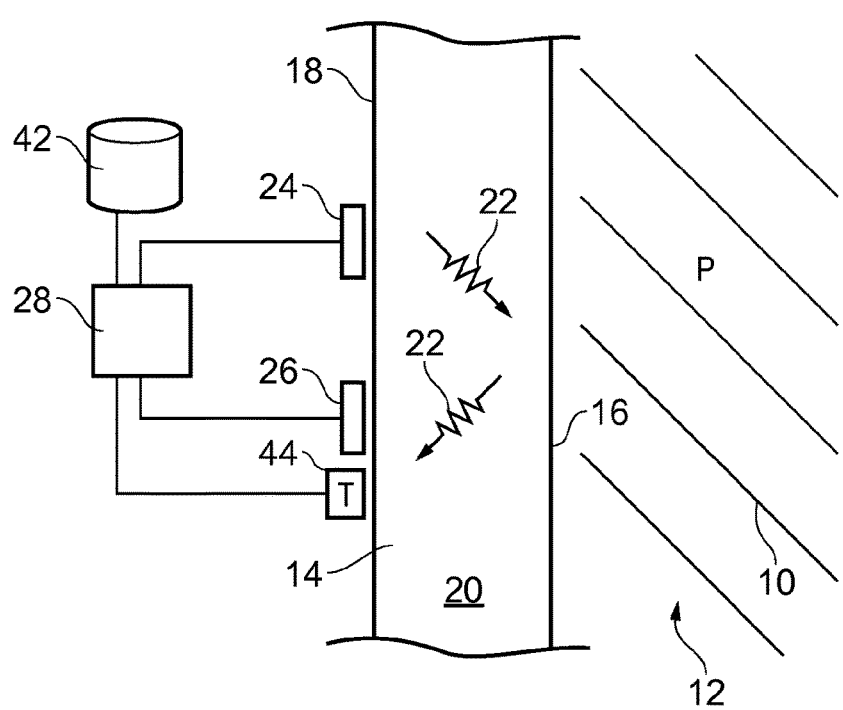

In the example of FIG. 2, ultrasound 22 is created and detected by respective transducers 24, 26. The transmitter 24 and the receiver 26 are both positioned at the outer surface 18. The transmitter 24 introduces ultrasound into the body 20 to propagate across the body to the inner surface 16 and then to reflect from the inner surface 16, before propagating back to the receiver 26 for detection. This allows a measurement to be made of the total time of flight from the introduction position at the transmitter 24, across to the inner surface 16 and back to the detection position at the receiver 26.

In this example, the body 20 is a metal, such as stainless steel. The transducers are 10 MHz ultrasound transducers cemented to a region of the outer surface 18 which has been given a mirror finish to allow low noise ultrasound to be introduced into and detected from the body 20. Examples include piezoelectric transducers.

The transmitter 24 and receiver 26 are connected with a control arrangement 28 which may consist of bespoke electronic circuits, or a suitably programmed general purpose computer communicating with the transmitter 24 and receiver 26 through appropriate interface circuits.

Figure 3:
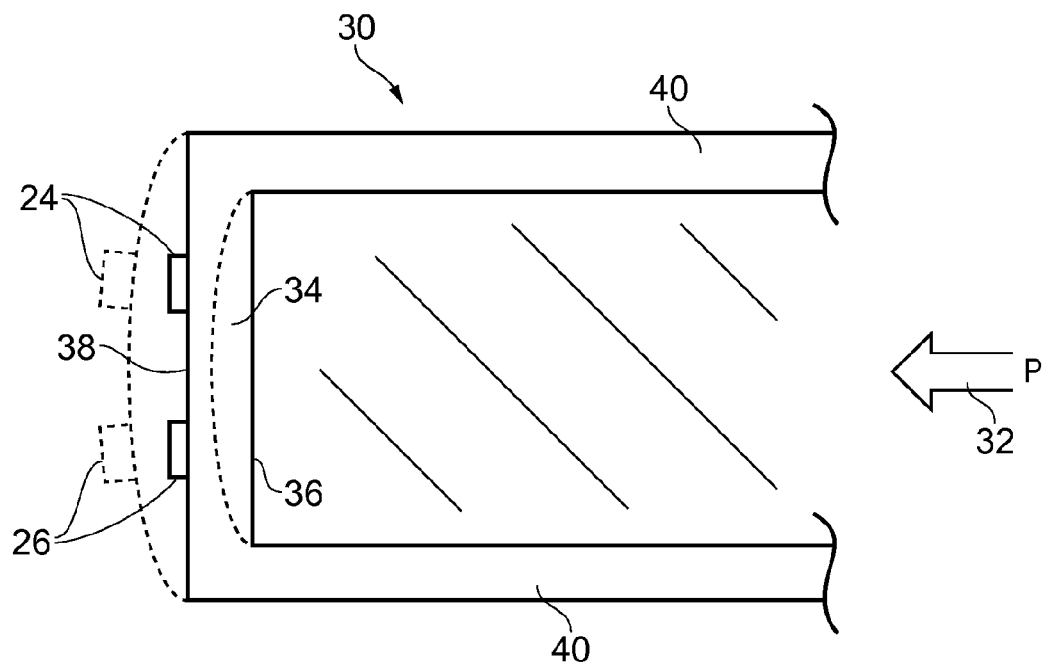
FIG. 3 is a simple sectional view through an experimental rig used to demonstrate an example of the invention.

Operations of the control arrangement 28 will be further described after discussing FIG. 3.

FIG. 3 illustrates an idealised chamber 30 containing fluid which is exposed at 32 to pressure P. The chamber 30 has an end wall 34 which may be of stainless steel. The end wall 34 has a relaxed form indicated by solid lines in FIG. 3, and which will be mechanically influenced by the pressure P. One example of the form of the end wall 34, when under pressure, is indicated on a highly exaggerated basis by broken lines in FIG. 3.

Prior to the application of the pressure P, when the end wall 34 is in a relaxed condition, the inner surface 36 and the outer surface 38 are both flat and parallel in this example. When the additional pressure P is applied, a pressure differential arises across the wall 34. This is illustrated as causing deformation of both surfaces 36, 38 of the wall 34. This creates mechanical stresses within the material of the end wall 34. In other examples, one surface 36, 38 may deform without the other being deformed. The thickness of the wall 34 (the separation of the surfaces 36, 38) may change as a result of compression of the material of the wall 34, with or without a change of shape.

The side walls 40 will also be mechanically influenced by deformation or compression, in a similar manner, but this is not illustrated in FIG. 3, for simplicity.

The end wall 34 is provided with a transmitter 24 and receiver 26, corresponding with those illustrated in FIG. 2. Consequently, by considering FIG. 2 and the description above, it can be seen that the transmitter 24 in FIG. 3 can introduce ultrasound into the material of the wall 34, at the outer surface 38, this ultrasound then propagating through the end wall 34 to the inner surface 36 and then reflecting back through the body of the end wall 34, to the receiver 26. This allows a measurement to be made for the total time of flight from the transmitter 24 to the receiver 26, by reflection from the inner surface 36.

Figure 4:
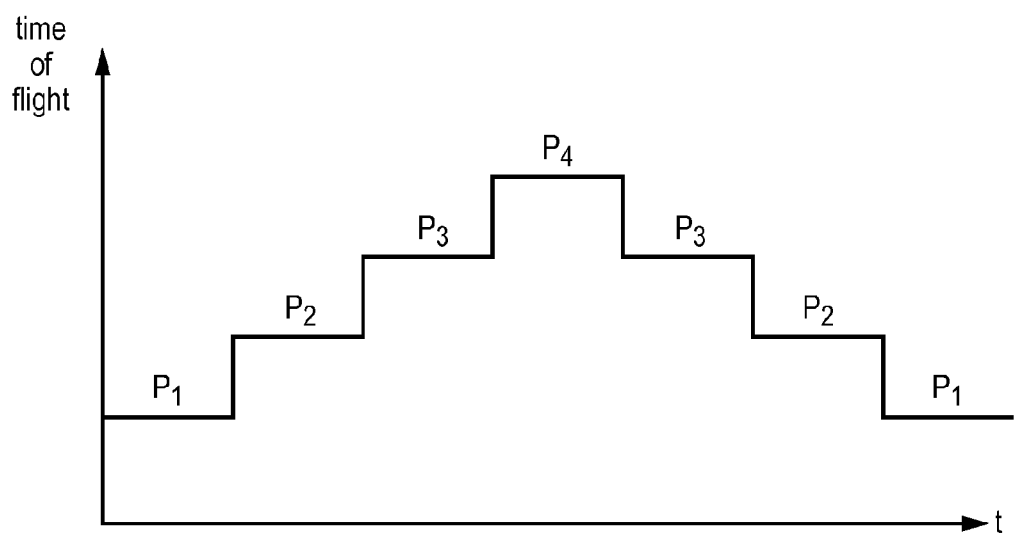
FIG. 4 is a plot of fluid pressure measurements obtained from the experimental rig of FIG. 3.

We have found that the time of flight which is measured in this way will change as the pressure P changes. FIG. 4 shows results measured from an experimental rig having the geometry of FIG. 3, for which the pressure P can be controlled. Constant temperature was maintained for the chamber 30, while capturing the data illustrated in FIG. 4. The horizontal axis represents time. Measurements of the time of flight were repeatedly taken, generating horizontal traces on the plot of FIG. 4. Periodically, the pressure within the rig was changed. On each occasion, this resulted in a step change in the measured time of flight, as can be seen from the step changes in the traces of FIG. 4. The pressure within the rig is indicated as $P_1$, $P_2$ etc. adjacent each step of the plot of FIG. 4. It is to be noted that the pressure can be changed to increase or decrease the time of flight, in a repeatable manner, indicating that the phenomenon is based on elastic changes, rather than plastic deformation.

Returning now to FIG. 2, it can be understood that the experimental data shown in FIG. 4 can be used for calibration of measurements taken in the arrangement illustrated in FIG. 2, if the experimental rig from which the data was collected corresponds in all relevant respects (material, geometry, temperature and other parameters) with the environment in which the apparatus of FIG. 2 is used. Alternatively, calibration data may be acquired by taking calibration measurements from the arrangement of FIG. 2, while the pressure P is controlled and known. Calibration data corresponding with FIG. 4 is stored at 42 to be accessible by the control arrangement 28. The control arrangement 28 is able to initiate a measurement by instructing the transmitter 24 to introduce ultrasound into the body 20, and for the receiver 26 to listen for the echo received from the inner surface 16. This allows the control arrangement 28 to measure the time of flight across the body 20 and back to the receiver 26. A measured time of flight is then compared by the control arrangement 28 with the calibration data at 42 in order to provide a measurement of the fluid pressure at the inner surface 16, as a function of the time of flight measurement. In the event that the calibration data 42 is also calibrated against other parameters such as temperature, it will be necessary for the control arrangement 28 to be provided with additional information from appropriate sensors such as a temperature sensor 44.

Explanatory Discussion

Returning to FIG. 3, it has been noted above that as the pressure P increases, the end wall 34 deforms by ballooning outwardly, creating stress within the material of the wall 34. Stress within a material such as a metal (stainless steel, for example) is understood to affect the acoustic velocity of ultrasound. Thus, stress within the material is expected to be a factor causing a change in the time of flight of ultrasound crossing the wall 34 between the inner surface 36 and the outer surface 38. In the situation of FIG. 3, the compressive forces exerted by the pressure P will also have the effect of compressing the material of the wall 34 and thus reducing the thickness of the wall 34. This will reduce the path length for ultrasound passing through the thickness of the wall (between the outer surface 38 and the inner surface 36). Thus, the compression of the wall thickness will be a factor causing a reduction in the time of flight of ultrasound crossing the wall 34 between the inner surface 36 and the outer surface 38.

We have realised that in many practical situations in which pressurised fluid is contained by a metal wall, changes in fluid pressure will result in changes in these two factors of material stress and wall thickness. These factors are both understood to influence the time of flight. There may be other factors which also affect time of flight as the fluid pressure changes. The changes which will occur in a particular situation may be difficult to identify, calculate or model, but will be measurable in many practical situations. Calibration measurements, taken as described above and then recorded for future reference, will allow the measurable changes in time of flight to be used to measure the fluid pressure. Accordingly, although the geometry shown in FIG. 3 may be much simpler than many geometries which are encountered in practice within machines and machine components, we believe that the principles described above will nevertheless be applicable, particularly if calibration measurements are taken and if other factors which can affect time of flight (such as temperature) are kept constant, or are incorporated within the calibration data.

Bearings

Figure 5:
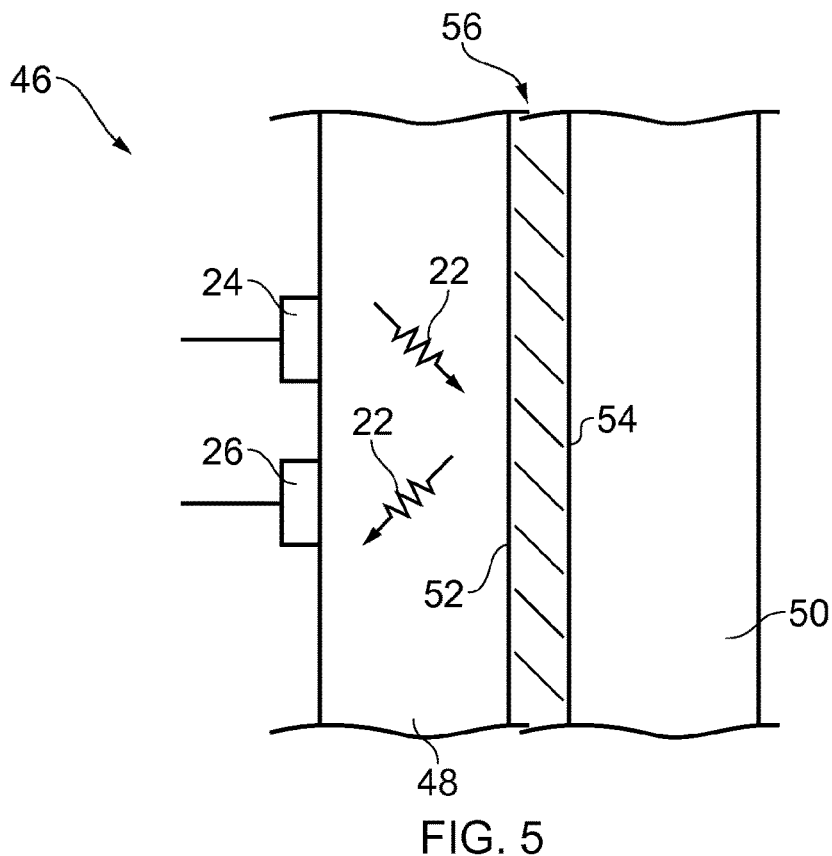
FIG. 5 illustrates an example of the invention in use with a fluid film bearing of a machine.

The remaining drawings illustrate examples of practical situations in which the principles described above can be applied. FIG. 5 illustrates a section through part of a bearing 46 which has a first bearing component 48 and a second bearing component 50. These respectively have surfaces 52, 54 which move relative to each other during use and are lubricated by a lubricating fluid 56. The fluid 56 will be under pressure during use. The fluid 56 will therefore apply pressure to the first bearing component 48, resulting in the first component 48 being affected in the manner described above in relation to FIG. 3. Accordingly, the use of a transmitter 24 and receiver 26 will allow ultrasound 22 to be introduced into the first component 48 in order to measure the pressure of the fluid 56, in the manner described above. The control arrangement 28 and associated structures are omitted from FIG. 5, for clarity.

Combustion Chamber

Figure 6:
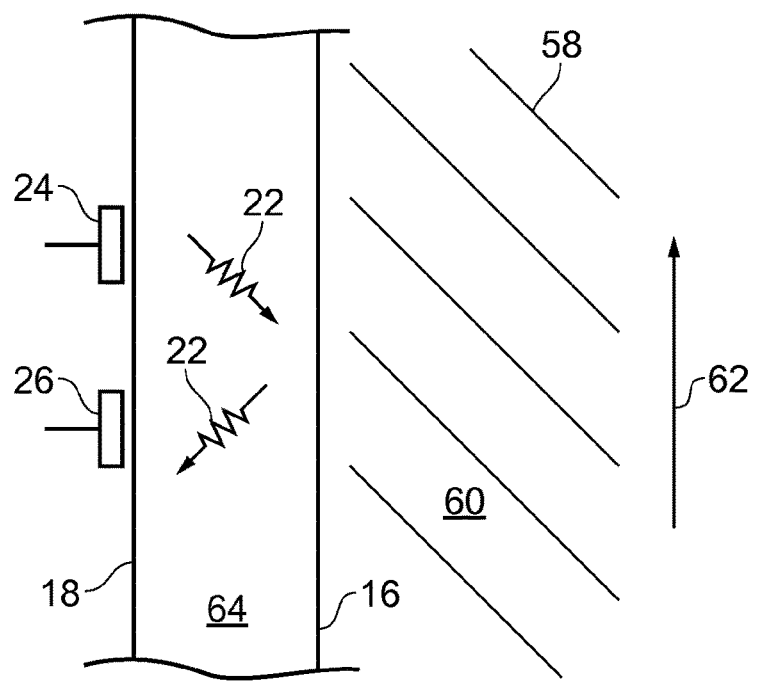
FIG. 6 illustrates an example of the invention in use with a combustion chamber of a machine.

Another example of a practical implementation is shown in FIG. 6. This illustrates combustion gases 58 (indicated by hatching) in a combustion chamber 60. The combustion gases 58 may be flowing, as indicated by the arrow 62. The pressure of the combustion gases 58 will be exerted on the inner surface 16 of the combustion chamber wall 64. Thus, a transmitter 24 and receiver 26 can again be used at the outer surface 18 of the wall 64 in order to measure the pressure of the combustion gases 58 within the chamber 60. In this example, the likely high and variable temperatures within the combustion chamber 60 will make it desirable for calibration measurements to be taken at various different temperatures, and for the control arrangement 28 (not shown in FIG. 6) to be provided with data from appropriate temperature sensors (not shown). Calibration for temperature changes is expected to be achieved more simply in situations where the rate of thermal conductivity in the chamber wall 64 is much slower than the rate of stress propagation caused by pressure changes.

CONCLUDING REMARKS

We expect that the high frequency and high velocity of ultrasound in metals typically used for manufacturing machines and machine components will allow pressure measurements to be made in the manner described above, sufficiently accurately to allow the pressure measurement to be used for a variety of monitoring and control purposes in real-time, while the machine or machine component is in use.

Many variations and modifications can be made to the apparatus described above, without departing from the scope of the invention. Bodies of metal have been described in several different examples. The metal may be multiple layers of different materials. For example, bearings are typically constructed of multiple layers of different materials. They may be tri-metallic (such as iron/copper/lead). The use of the term "metal" in this specification is intended to encompass metal alloys. Other materials can be used.

Separate transducers have been described for ultrasonic transmission and reception. A single transducer could alternatively be used (as a transceiver). In that case, the introduction position and the detection position would be the same.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. A method of measuring the pressure of a contained fluid, the fluid being contained in a chamber which is defined, at least in part, by a first side wall, a second side wall, and an end wall each having an inner surface exposed to the fluid within the chamber, wherein the inner surface of the first side wall opposes the inner surface of the second side wall across the chamber, the end wall further having an outer surface separated from the inner surface of the end wall by the material of the end wall, the method comprising:
   providing the end wall to have inner and outer surfaces which are flat and parallel when the end wall is in a relaxed condition, wherein the inner surface of the end wall extends between the inner surface of the first side wall and the inner surface of the second side wall;
   introducing ultrasound into the material of the end wall at an introduction position;
   detecting the ultrasound after travelling through the material of the end wall to a detection position;
   measuring the time of flight of the detected ultrasound from the introduction position to the detection position; and providing a measurement of the fluid pressure at the inner surface of the end wall, as a function of the measured time of flight.

2. A method according to claim 1, wherein the fluid pressure measurement is provided by comparison of the time of flight measurement with previously calibrated measurements of fluid pressure and time of flight.

3. A method according to claim 1, wherein the ultrasound is introduced at one surface of the end wall and travels to the other surface of the end wall.

4. A method according to claim 3, wherein the ultrasound reflects from the other surface of the end wall and is detected at the said one surface of the end wall.

5. A method according to claim 3, wherein the ultrasound is introduced at the outer surface of the end wall.

6. A method according to claim 1, wherein the material of the end wall is metal.

7. A method according to claim 1, wherein the end wall and chamber form part of a machine or machine component.

8. A method according to claim 7, wherein the machine or machine component comprise one or more of a combustion chamber, a bearing, a gearbox and a cam arrangement.

9. A method according to claim 1, wherein the fluid is a lubricant, compression fluid or actuator fluid.

10. A method according to claim 1, wherein, when the end wall is in a relaxed condition, the inner surface of the end wall which extends between the inner surface of the first side wall and the inner surface of the second side wall is planar.

11. A method according to claim 1, wherein, when the end wall is in a relaxed condition, the inner surface of the end wall which extends between the inner surface of the first side wall and the inner surface of the second side wall is continuously flat.

12. Apparatus comprising a chamber which, in use, contains fluid, the chamber being defined, at least in part, by a first side wall, a second side wall, and an end wall each having an inner surface exposed to the fluid within the chamber, wherein the inner surface of the first side wall opposes the inner surface of the second side wall across the chamber, the end wall further having an outer surface separated from the inner surface of the end wall by the material of the end wall, the apparatus further comprising:
   an ultrasound transducer arrangement operable to introduce ultrasound into the material of the end wall at an introduction position and to detect the ultrasound after travelling through the material of the end wall to a detection position;
   a control arrangement operable to measure the time of flight of the detected ultrasound from the introduction position to the detection position and to provide a measurement of the fluid pressure at the inner surface of the end wall, as a function of the measured time of flight;
   and wherein the inner surface and the outer surface of the end wall are both flat and parallel when the end wall is in a relaxed condition, wherein the inner surface of the end wall extends between the inner surface of the first side wall and the inner surface of the second side wall.

13. Apparatus according to claim 12, wherein the control arrangement provides the fluid pressure measurement by comparison of the time of flight measurement with previously calibrated measurements of fluid pressure and time of flight.

14. Apparatus according to claim 13, wherein the ultrasound transducer arrangement is operable to introduce ultrasound at the outer surface of the end wall.

15. Apparatus according to claim 12, wherein the ultrasound transducer arrangement is operable to introduce at one surface of the end wall and travels to the other surface of the end wall.

16. Apparatus according to claim 15, wherein the ultrasound transducer arrangement is operable to cause ultrasound to reflect from the other surface of the end wall and be detected at the said one surface of the end wall.

17. Apparatus according to claim 12, wherein the end wall and chamber form part of a machine or machine component.

18. Apparatus according to claim 17, wherein the machine or machine component comprise one or more of a combustion chamber, a bearing, a gearbox and a cam arrangement.

19. Apparatus according to claim 12, wherein the fluid is a lubricant, compression fluid or actuator fluid.

20. A method of measuring the pressure of a lubrication fluid in a bearing, the lubrication fluid being disposed between a first bearing component and a second bearing component which, in use, move relative to each other, the first bearing component and the second bearing component each having an inner surface exposed to the lubricating fluid between the first bearing component and the second bearing component, and an outer surface separated from the respective inner surface by the material of the respective first bearing component or second bearing component, the method comprising:
   introducing ultrasound into the material of the first bearing component at an introduction position;
   detecting the ultrasound after travelling through the material of the first bearing component to a detection position;
   measuring the time of flight of the detected ultrasound from the introduction position to the detection position;
   and providing a measurement of the lubrication fluid pressure at the inner surface of the first bearing component, as a function of the measured time of flight.

* * * * *